United States Patent [19]
Buess et al.

[11] Patent Number: 5,219,348
[45] Date of Patent: Jun. 15, 1993

[54] COAGULATION, SUCTION AND WASHING INSTRUMENT

[75] Inventors: Gerhard F. Buess, Tübingen; Andreas Melzer, Wiesbaden; Manfred Boebel, Oetisheim; Dieter Metsch, Kraichtal-Ba, all of Fed. Rep. of Germany

[73] Assignee: Richard Wolf GmbH, Knittlingen, Fed. Rep. of Germany

[21] Appl. No.: 874,944

[22] Filed: Apr. 28, 1992

[30] Foreign Application Priority Data

Jun. 14, 1991 [DE] Fed. Rep. of Germany ....... 4119592

[51] Int. Cl.$^5$ ............................................. A61B 17/39
[52] U.S. Cl. ...................... 606/49; 606/32; 606/40; 606/45
[58] Field of Search .................... 606/32-50

[56] References Cited

U.S. PATENT DOCUMENTS

| | | | |
|---|---|---|---|
| 3,532,095 | 10/1970 | Miller | 606/49 X |
| 4,562,838 | 1/1986 | Walker | 606/49 X |
| 5,015,227 | 5/1991 | Broadwin et al. | 606/49 X |
| 5,071,418 | 12/1991 | Rosenbaum | 606/45 X |
| 5,085,657 | 2/1992 | Ben-Simhon | 606/49 X |
| 5,088,997 | 2/1992 | Delahuerga et al. | 606/49 X |
| 5,098,430 | 3/1992 | Fleenor | 606/49 X |
| 5,133,714 | 7/1992 | Beane | 606/49 |
| 5,154,709 | 10/1992 | Johnson | 606/49 X |
| 5,167,659 | 12/1992 | Ohtomo et al. | 606/49 X |

Primary Examiner—Peter A. Aschenbrenner
Attorney, Agent, or Firm—Panitch, Schwarze Jacobs & Nadel

[57] ABSTRACT

A coagulation, washing and suction instrument has a shaft having a washing and a suction canal, by way of which a washing fluid can be supplied to, or removed from, respectively, a bodily cavity. The instrument consists of three detachably connected parts, namely a shaft having a washing and a suction canal; a handle which can be pushed onto, and secured to, the proximal end of the shaft, the handle being made of an insulating material and having a high frequency connector for supplying a coagulation electrode on the distal end of the shaft, and finger pressure releasable connection canals for the supply to, and the removal from, the canals of the shafts, of the washing fluid; and a part for the introduction of auxiliary instruments, which can be coupled proximally to the shaft and to the handle and which can be shut off.

7 Claims, 2 Drawing Sheets

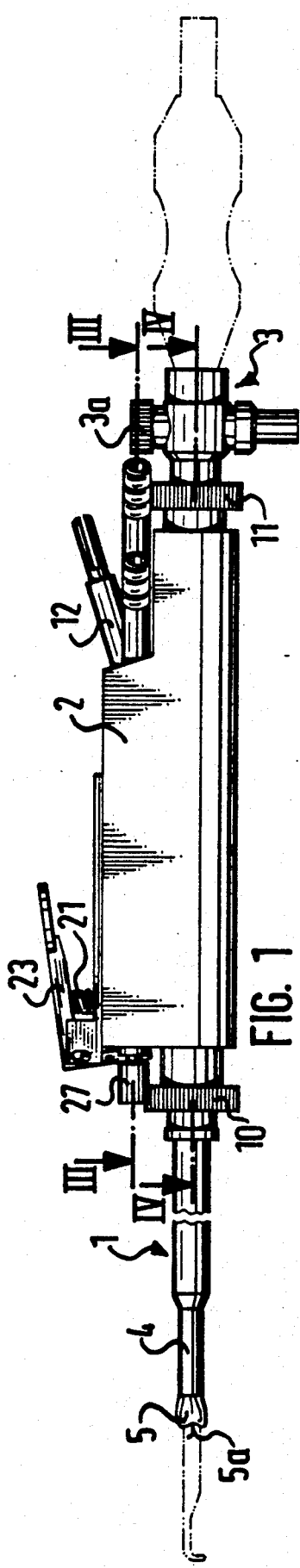
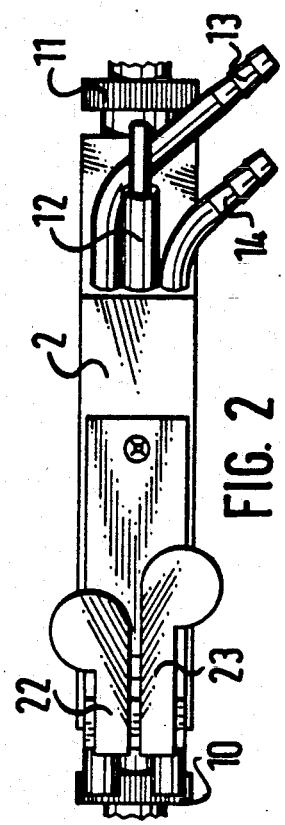
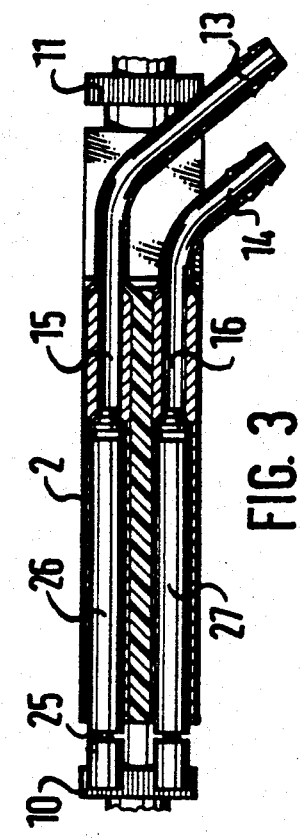
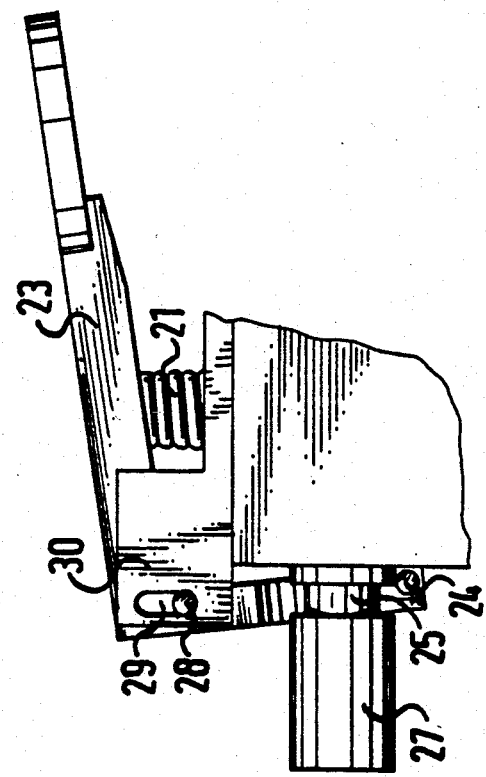

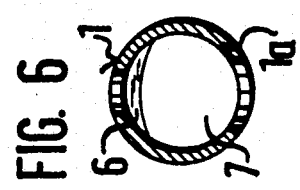
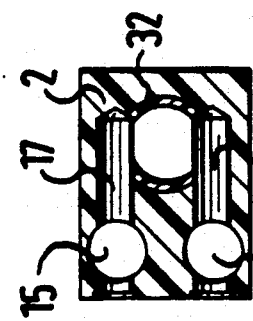
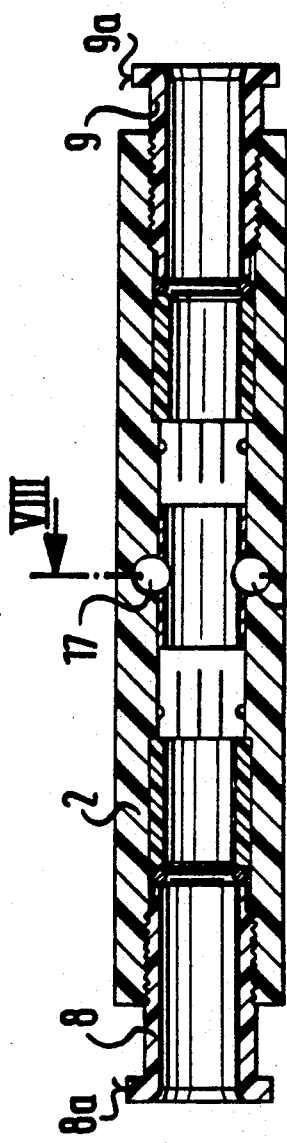
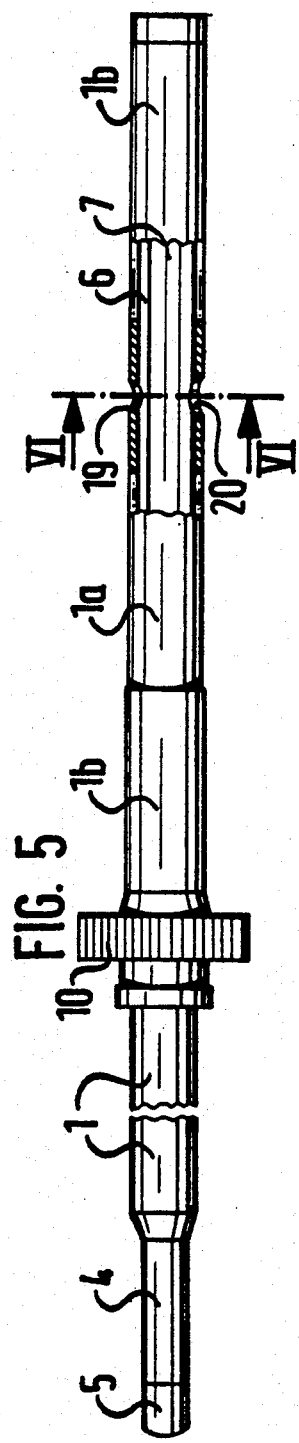
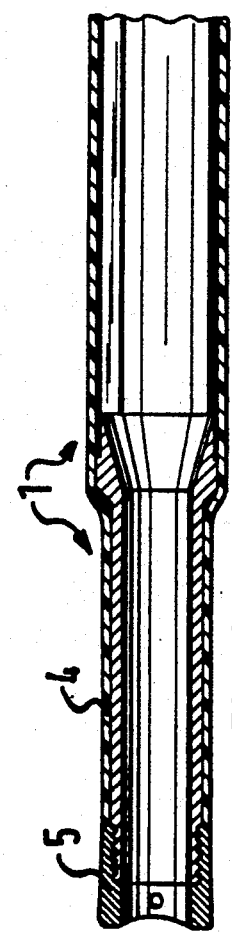

5,219,348

COAGULATION, SUCTION AND WASHING INSTRUMENT

FIELD OF THE INVENTION

This invention relates to a coagulation, suction and washing instrument having a shaft defining a washing and a suction canal, for the introduction into, and the removal from, a bodily cavity, of a washing fluid.

BACKGROUND OF THE INVENTION

In known instruments of the type recited above a handle is provided as a fixed non-detachable part of the instrument. If a second puncture into the bodily cavity must be made whilst treating a patient, when, for example, additional auxiliary instruments need to be brought to the site of the operation in the bodily cavity, the main instrument must be exchanged for another such instrument.

SUMMARY OF THE INVENTION

The present invention is intended to provide, in the case of difficult endoscopic operations, in particular in a confined space, the facility to bring auxiliary instruments into use, without changing over the main instrument and without the need to make a second puncture at the site of the operation, the instrument also being easy to handle.

According to the present invention a coagulation, washing and suction instrument with a shaft having a washing and suction canal for the supply and removal of a washing fluid into and out of a bodily cavity, comprises three detachably connected parts; namely a shaft with a washing and a suction canal; a handle which can be pushed onto, and secured on, the proximal end of the shaft, which handle is made of insulating material and has a high frequency connection to the shaft, and connection canals which can be released by finger pressure, for the supply and removal of the washing fluid to the two shaft canals; and an introduction part which can be coupled proximally to the shaft and to the handle and can be shut off, for auxiliary instruments which are to be passed through the shaft.

The instrument may be so constructed that it can be used by either a right-handed or a left-handed operator

BRIEF DESCRIPTION OF THE DRAWINGS

FIG. 1 is a side view of a coagulation, washing and suction instrument according to a preferred embodiment of the invention;

FIG. 2 is a top plan view of a handle part of the instrument;

FIG. 3 is a longitudinal sectional view taken on the lines III—III of FIG. 1;

FIG. 4 is an enlarged longitudinal sectional view taken on the lines IV—IV of FIG. 1;

FIG. 5 is a side view of a shaft of the instrument shown partly in longitudinal section;

FIG. 6 is a cross-sectional view taken on the lines VI—VI of FIG. 5;

FIG. 7 is an enlarged side view of a distal handle part of the instrument showing valve actuating means;

FIG. 8 is a cross-sectional view taken on the lines VIII—VIII of FIG. 4; and

FIG. 9 is an enlarged sectional view through the distal part of the shaft of the instrument.

DETAILED DESCRIPTION OF THE PREFERRED EMBODIMENT OF THE INVENTION

An instrument for coagulating tissue, introducing washing fluids into, and removing such fluids and bodily secretions from, a body cavity, comprises an instrument shaft 1, having a distal end 4 of reduced diameter, a coagulation electrode 5 joined thereto and terminating in a concave recess 5a with an open end face, a handle 2 of insulating material, and an instrument introduction part 3 provided with a trumpet valve 3a which can be closed. The part 3 is for the introduction of an auxiliary instrument to be guided through the shaft 1 and into a bodily cavity.

The shaft 1 is divided into two longitudinal canals 6 and 7 (FIGS. 5 and 9). The canal 6 is for the introduction of washing fluid into the body cavity and is of smaller cross-sectional area than the canal 7, which is for the passage of the auxiliary instrument and for use in the removal of said washing fluids and bodily secretions.

The proximal end of the shaft 1 is inserted into a central channel in the handle 2 and is secured therein. Both ends of said central channel are screw threaded and threadably receive insulating sleeves 8 and 9, respectively. The ends of the sleeves 8 and 9, have screw threads 8a and 9a respectively, at their ends remote from the handle 2. When the proximal end of the shaft 1 has been inserted into the central channel of the handle 2, the shaft 1 is secured to the handle 2 by means of a screw threaded ring 10 meshed with the screw thread 8a.

The proximal instrument introduction part 3 is connected firmly and securely to the handle 2 by means of a screw threaded ring 11 meshed with the screw thread 9a. A tube 1a is non-detachably secured to the shaft 1 between two cylindrical insulating sleeves 1b thereon, only one of which is shown.

The upper side of the handle 2 is provided with a high frequency connector 12 connected to the externally insulated shaft 1 by means of contact rings in the handle 2. When the instrument is in use, high frequency current is supplied to the distal coagulating electrode 5. The canals 6 and 7 of the shaft 1 are connected to fluid supply and suction lines 13 and 14, respectively, by way of longitudinal canals 15 and 16 respectively, and transverse canals 17 and 18, respectively, in the handle 2, as best seen in FIG. 8. To this end, the walls of the canals 6 and 7 have perforations 19 and 20, respectively, communicating with the canals 17 and 18, respectively, when said proximal end of the shaft 1 is inserted into the handle 2.

Angled switching levers 22 and 23 are mounted on the handle 2 for controlling the supply and removal of the washing fluid. Each lever 22 and 23 is actuable against the action of a spring 21. A follower pin 24 connected to the levers 22 and 23 engages in an annular groove 25 of valve tappets 26 and 27. By pressing the lever 22, the tappet 26 is withdrawn from its closure position so that washing fluid can flow by way of the line 13 and the canals 15 and 17, the perforation 19 and the canal 6 of the shaft 1, into a body cavity to be treated. When the lever 22 is released, the through flow of the fluid is interrupted automatically, since the spring 21 returns the lever 22 to its starting position, the tappet 26 being simultaneously returned to its closure position. When the lever 23 is pressed the tappet 27 is actuated so that the washing fluid is removed from the body cavity with any bodily secretions there may be, by way of the canal 6 and the suction line 14. The actuation of the levers 22 and 23, therefore, causes axial displacement of the tappets 26 and 27 and thus the introduction or the drawing off of fluid and release of the levers 22 and 23, conversely, closes off the canals.

The insulating sleeves 8 and 9 secured in the canal of the handle 2 are equally spaced from the perforations 19 and 20 and the transverse canals 17 and 18, whereby said proximal end of the shaft 1 may be introduced through the sleeve 8 or the sleeve 9 into the handle 2, so that the handle 2 can be adapted for use either by a right-handed, or a left-handed operator.

The canal 7 of the shaft 1 ends distally in the shaft 1 in front of its reduced diameter or constricted distal end 4. The open distal end of the shaft 1 can accordingly be brought to rest against an organ of the body, so as to close said open end. The washing fluid can now be supplied by way of the canal 6 and drawn off by way of the canal 7 in front of said constricted end, in order to wash free the canal 7, if it is obstructed, for example by bodily secretions, without having to remove the instrument from said cavity. This washing operation may be effected when an auxiliary instrument is passed through the canal 7.

By virtue of the construction described above the shaft 1, the handle 2 and the instrument introduction part 3 can readily be assembled and dismounted. Cleaning and disinfecting of those parts is, therefore, facilitated. Also to this end the two tappet valves 26 and 27 can also be removed from the handle 2, by removing the follower pin 24 from the groove 25. In order to allow of this the end of each switching lever 22 and 23 which end is secured in a rocker arm 29 by means of a pin 28, is displaced at an angle vertically with respect to the longitudinal axis of the instrument until the pin 24 is withdrawn from the annular groove 25, the said end being detachably secured in this position by means of a ball catch (not shown), for example, in the bearing 30 of the levers 22 and 23. If the switching lever 22 or 23 is in the lower position shown in FIG. 7, with the pin 24 within the rocker arm 29, then the pin 24 is pressed against the handle 2 by the action of the spring 21, so that additional fixing elements are not needed.

The shaft 1 may be turned through a predetermined angle about said longitudinal axis, so that the canal 7 is connected to the fluid supply line 13, the canal 15 and the perforation 19, for washing free the canal 7.

The recess 5a at the distal end of electrode 5 enables the instrument to be used for coagulating bodily tubes such as blood vessels, the recess 5a restraining the electrode 5 from sliding off the said bodily tube.

What is claimed is:

1. A coagulation, washing and suction instrument for supplying washing fluid to a bodily cavity and for removing such fluid therefrom, said instrument comprising:

a shaft defining a washing and a suction canal, the shaft having a proximal end and a distal end and a coagulation electrode at said distal end;

a handle made of an insulating material and adapted to be pushed onto, and detachably secured to, the proximal end of the shaft, the handle having a high frequency connector for the supply of high frequency current to the coagulation electrode, canals for connection to said supply and suction canals for the supply to and the removal from, said bodily cavity of said washing fluid, and means operable by finger pressure for opening and closing said connection canals; and an instrument introduction part for releasable coupling proximally to the shaft and the handle, for the passage of auxiliary instruments through the shaft, said introduction part being capable of being closed off.

2. An instrument as claimed in claim 1, wherein the handle defines a channel for receiving the proximal part of the shaft, for the introduction and securing of said proximal part in said channel, a cylindrical insulating sleeve being received in each of two opposite ends of said channel, one insulating sleeve having a screw threaded free end for meshing with a screw threaded ring for securing said shaft to the handle and the other insulating sleeve having a screw threaded free end for securing the instrument introduction part to the handle.

3. An instrument as claimed in claim 1, wherein said connection canals are connected to a fluid supply line and to a fluid suction line, respectively, and are connectable by way of further canals to the said washing canal and said suction canal, respectively, of said shaft, the handle having axially displaceable valve tappets for opening and closing said canals and spring loaded switching levers mounted on the handle for actuating said tappets to open and close said canals.

4. An instrument as claimed in claim 1, comprising a pair of switching levers mounted on the handle for actuating valves for opening and closing the washing and the suction canals and said connection canals, each lever being movable into a canal opening position against the action of a spring urging the lever towards a canal closing position.

5. An instrument as claimed in claim 1, wherein said suction canal is of greater cross-sectional area than said washing canal, for the passage of said auxiliary instruments through the shaft and terminates distally of a reduced cross-section distal end portion of the shaft.

6. An instrument as claimed in claim 1, wherein the walls of said washing and suction canals define perforations for communication with said connection canals.

7. An instrument as claimed in claim 6, wherein the handle defines a channel for receiving the proximal part of the shaft for the introduction and securing of said proximal part in said channel, an insulating sleeve being secured in each of two opposite ends of said channel and having a screw threaded end remote from said handle, the screw threaded ends of the said sleeves being equally spaced from said connection canals and said perforations.

* * * * *